United States Patent [19]

Fletcher

[11] Patent Number: 5,326,447
[45] Date of Patent: Jul. 5, 1994

[54] OXYGEN ANALYZER

[75] Inventor: Kenneth S. Fletcher, Rehoboth, Mass.

[73] Assignee: The Foxboro Company, Foxborough, Mass.

[21] Appl. No.: 954,395

[22] Filed: Sep. 30, 1992

[51] Int. Cl.$^5$ ............................................ G01N 27/26
[52] U.S. Cl. ................................. 204/401; 204/406; 204/412; 204/415; 204/431; 204/432; 204/153.17
[58] Field of Search ............... 204/401, 406, 412, 415, 204/431, 432, 153.17

[56] References Cited

U.S. PATENT DOCUMENTS

| 3,227,643 | 1/1966 | Okun et al. | 204/195 |
| 3,420,764 | 1/1969 | Schlein | 204/195 |
| 3,432,418 | 3/1969 | Kleiss | 204/195 |
| 3,857,771 | 12/1974 | Sternberg | 204/431 |
| 4,207,146 | 1/1980 | Kunke | 204/403 |
| 4,464,230 | 8/1984 | Langdon | 204/406 |
| 4,900,422 | 2/1990 | Bryan et al. | 204/415 |
| 5,215,644 | 6/1993 | Ashikaga | 204/431 |

OTHER PUBLICATIONS

Smart et al., In Situ Voltammetric Membrane Ozone Electrode; 1979; *Analytical Chemistry;* vol. 51, No. 14, pp. 2315-1319.
Michael L. Hitchman; Measurement of Dissolved Oxygen; 1978; Zurich, Switzerland, Chapters 4 and 5, pp. 59-123.

*Primary Examiner*—John Niebling
*Assistant Examiner*—Bruce F. Bell
*Attorney, Agent, or Firm*—Fish & Richardson

[57] ABSTRACT

An analyzer for detecting a selected chemical (such as oxygen) in a process fluid includes a plurality of electrodes that are separated from the fluid by a membrane that is permeable to the selected chemical, each of the electrodes when energized producing a signal in response to the selected chemical in the fluid. The selected chemical level in the process fluid is determined based on the signal produced by a first one of the electrodes, and the determined level is used with the signal produced by a second one of the electrodes to detect whether the membrane has become faulty (e.g., fouled by materials in the process fluid).

47 Claims, 6 Drawing Sheets

OXYGEN ANALYZER

BACKGROUND OF THE INVENTION

This invention relates to analyzers for determining the level of a selected chemical in a process fluid.

A typical analyzer for measuring the level of a chemical in a process fluid includes a voltammetric sensor that supports one or more electrodes in electrolytic contact with the fluid. The electrodes are immersed in an electrolytic solution of fixed composition at one end of the sensor and are separated from the process fluid by a membrane that is permeable to the selected chemical This type of sensor is known as a Clark cell when the chemical to be measured is oxygen or its allotropes such as ozone.

When the sensor is inserted in the process fluid and an oxygen-permeable membrane is used, oxygen in the fluid diffuses through the membrane into the electrolytic solution. As a result, when the electrodes are energized (with either D.C. or pulsed potential) they produce an electrical signal that is proportional to the level of oxygen in the electrolyte, and hence the amount of oxygen in the process fluid.

Such sensors may be adversely affected by membrane breakage or fouling. For example, the membrane may become fouled during use by materials (such as dirt, oil, grease, sludge, etc.) in the process fluid that collect on the membrane, reducing its permeability. As a result, the signal produced by the sensor will no longer accurately reflect the oxygen level in the process fluid, thereby leading to measurement errors. This problem is particularly acute when the process fluid comprises sludge-laden waste water in sewage treatment plants.

SUMMARY OF THE INVENTION

This invention provides an efficient and highly accurate technique for determining whether the sensor membrane has become faulty by providing the sensor with multiple electrodes—one of which is used to measure the level of a selected chemical in the process fluid, and another electrode serving as a diagnostic device that enables faults in the membrane to be detected In one general aspect of this concept, the signal produced by a first electrode when energized is used to determine the selected chemical level of the process fluid, and the signal produced by a second electrode when energized is used in conjunction with the determined level to detect whether the membrane is faulty.

Preferred embodiments include the following features.

The signal produced by the second electrode is analyzed to derive an expected level of the selected chemical (which is, e.g., oxygen or an allotrope thereof, such as ozone). The membrane is detected to be faulty if the oxygen level as determined from the signal produced by the first electrode differs from the expected level by more than a selected amount. Preferably, a portion of the signal produced by the second electrode is integrated to produce the expected level. The selected amount is based on a calibrated ratio between the determined level and the expected level and is between 10% and 50% of the calibrated ratio. An alarm is generated if the membrane is determined to be faulty.

The first and second electrodes are energized for mutually exclusive periods of time and for different durations. The first electrode is energized for longer durations than the second electrode. The first electrode is energized for a time sufficient to allow the signal that it produces to reach a steady-state value, while the amount of time that the second electrode is energized is insufficient to allow its signal to reach a steady-state value. For example, the first electrode is energized for intervals of 15 minutes or more, and the second electrode is energized on the order of 10 seconds between successive energizations of the first electrode. The user can select these durations The signal produced by the second electrode is analyzed during only a portion of the time that the second electrode is energized (e.g., between two and four seconds after the second electrode is energized).

During operation of the sensor, the membrane may become coated by materials in the fluid sample, and the membrane is subject to fouling if such material reduces the permeability of the membrane to oxygen. The membrane is designated as being fouled—and thus faulty—if the determined level and the signal produced by the second electrode differ by more than the selected amount.

The temperature of the fluid is also determined (e.g., by a thermistor, which measures the temperature of the electrolyte solution in which the electrodes are disposed). At least the signal produced by the first electrode is corrected according to temperature to provide the user with a temperature-compensated measurement of the oxygen level. The oxygen level is presented in any convenient form (e.g., as a concentration in parts-per-million (ppm) or as a percent saturation of the fluid with oxygen).

The first and second electrodes are spaced by an amount selected to allow each electrode to measure the amount of oxygen in different regions of the electrolyte without interference from the other electrode. Preferably, the electrodes are each annular and are disposed coaxially with respect to each other.

One embodiment of the invention features detecting breakage of the membrane. Because the process fluid typically has a different electrical resistance than the electrolyte within which the first and second electrodes are immersed, membrane breakage is detected by determining the electrical resistance between the electrodes and comparing the resistance to an expected (i.e., reference) value. If a discrepancy is found, the membrane is determined to be broken. The resistance measurement is made during the 10 second period that the second electrode is energized, but after the 2-4 second time window in which the signal from the second electrode is analyzed to diagnose membrane fouling.

The sensor also includes a third electrode (known as an auxiliary electrode) disposed within the electrolyte with the first and second electrodes for supplying electrical current to energize the first and second electrodes. A fourth, reference electrode is disposed adjacent to first and second electrodes, and the electrical current applied to the third electrode is controlled based on the electrical potential developed between the reference electrode and the energized first and second electrodes.

The electrical current for the third electrode is generated by a driver. Loss of the electrolyte solution increases the load on the driver, and thus the output voltage of the driver is monitored and compared with a threshold. If the threshold is exceeded, loss of the electrolyte is deemed to have occurred, and an alarm is activated to so notify the user.

The sensor includes a housing for supporting the first and second electrodes and the electrolyte solution in a cavity thereof, a portion of which is bounded by the membrane. A second membrane (called a diaphragm) bounds another portion of the cavity and is maintained at a tension less that a tension of the first membrane The slack diaphragm expands preferentially to the membrane in response to temperature-induced expansion of the electrolyte (and, to a lesser degree, the presence of bubbles in the electrolyte solution), thereby maintaining a fixed spacing between the oxygen permeable membrane and the electrodes.

The invention provides an accurate, real time technique for determining whether the membrane has become fouled without interfering with the oxygen level measurement in any significant way. Because the second electrode is energized for only brief periods between relatively long measurement cycles in which the first electrode is energized, the membrane fouling diagnosis is essentially transparent to steady-state measurement of the oxygen level provided by the first electrode. The user can select the tolerable degree of membrane fouling based on the environment in which the sensor is used.

Other features and advantages of the invention will become apparent from the following detailed description, and from the claims.

DESCRIPTION OF THE PREFERRED EMBODIMENTS

Figure 1:
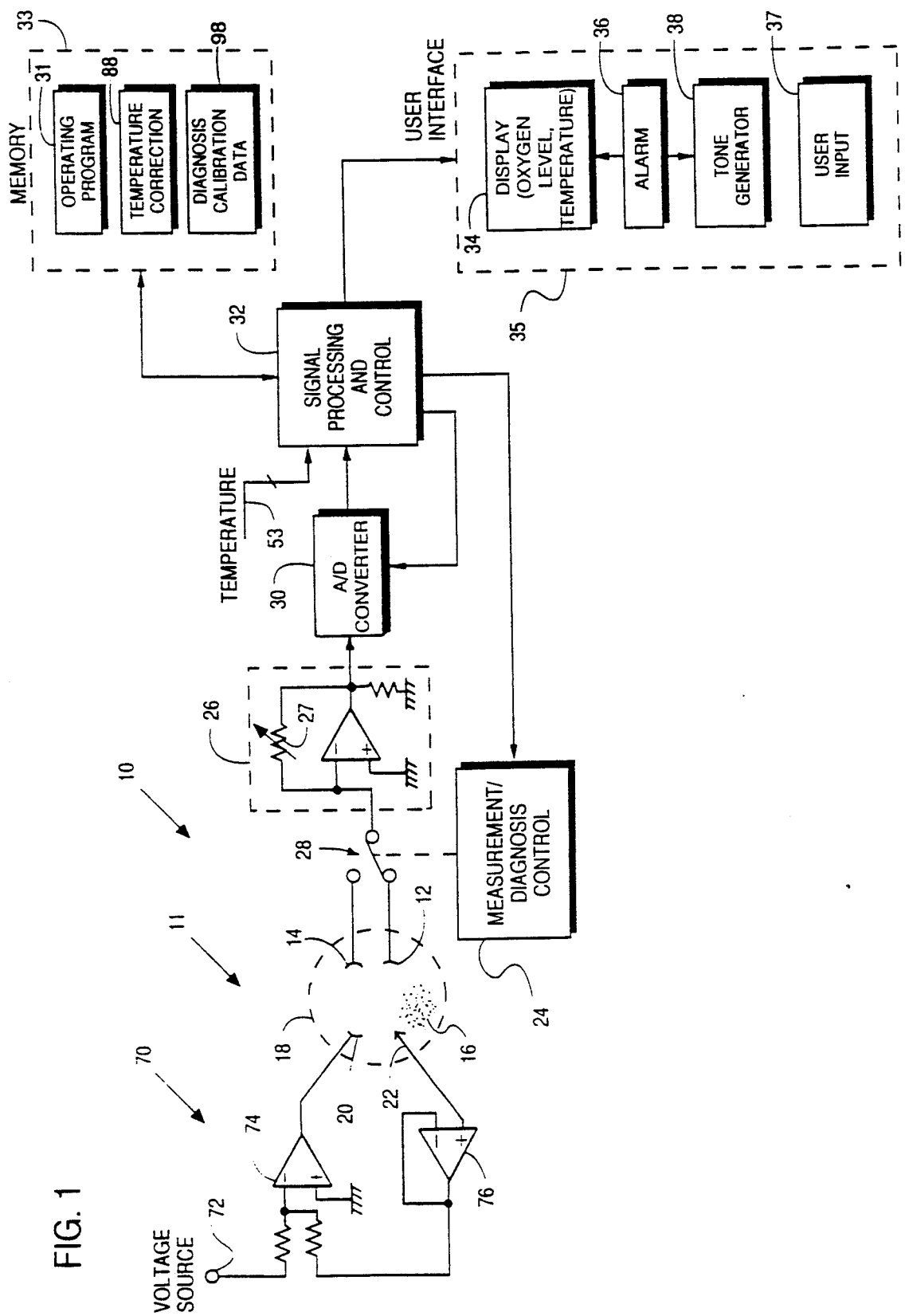
FIG. 1 is a functional block diagram of a chemical analyzer according to the invention, which includes a sensor for measuring the level of oxygen in a process fluid.

Referring to FIG. 1, an analyzer 10 for measuring the level of a selected chemical in a process fluid (not shown) includes a sensor 11 that contains a measurement electrode 12 and an adjacently disposed test electrode 14 immersed within an electrolyte solution 16 (only a portion of which is depicted) and enclosed by a membrane 18. Membrane 18 is permeable to the selected chemical, which is, for example, oxygen or its allotropes. Also enclosed by membrane 18 are an auxiliary electrode 20 for supplying energizing current to electrodes 12, 14, and a reference electrode 22 for allowing the voltage at electrodes 12, 14 to be maintained relatively constant for purposes to be described. Each electrode 12, 14 when energized produces an electrical current the amplitude of which is proportional to the level of oxygen that has diffused into the electrolyte solution from the process fluid.

Electrodes 12, 14 are selectively energized by measurement/diagnosis controller 24 at mutually exclusive times and for different durations. Controller 24 performs this function by selectively coupling electrodes 12, 14 to a current-to-voltage converter 26 (switch 28 schematically represents this function), which completes the electrical circuit with auxiliary electrode 20 and transforms the current produced by the selected electrode to a voltage that represents the level of oxygen in the process fluid. A variable resistor 27 in converter 26 allows the user to set the gain of the current to voltage conversion.

The voltage is digitized by an analog-to-digital (A/D) converter 30 and analyzed by a processor 32, which also controls the operation of controller 24 and A/D converter 30. Processor 32 operates under the control of a program 31 stored in memory 33. It will be appreciated that the functions of at least controller 24 and processor 32 can be implemented by a microprocessor; separate units are shown for ease of explanation.

The operation of analyzer 10 is discussed in detail below. Suffice it here to say that measurement electrode 12 is energized in a manner selected so that measurement electrode 12 produces a signal representative of the oxygen level in the process fluid, and test electrode 14 is periodically energized in place of measurement electrode 12 to develop a signal used by processor 32 in conjunction with the previously obtained signal from measurement electrode 12 to determine whether membrane 18 has become faulty (e.g. fouled or coated with material such as dirt, sludge, waste, oil, grease, etc.).

More specifically, measurement electrode 12 is energized for a time period sufficient to allow the current response thereof to reach a steady-state level. For example, electrode 12 is energized for between 15 minutes and 1 hour or more. As a result, in the absence of a fault in membrane 18 the current produced by electrode 12 (and hence the voltage applied to processor 32) is linearly related to the rate at which oxygen diffuses from the process fluid to electrolyte 16 across membrane 18, and thus the current is proportional to the oxygen level in the fluid. Processor 32 displays the measured oxygen level to the user (e.g., as a concentration in parts per million (ppm) or as a percent saturation) by illuminating a display 34 on user interface 35 (which is located, e.g., on the front panel of a housing that contains the circuitry discussed above). Alternatively, the measured oxygen level may be sent to a process control computer for adjusting the oxygen level in the process fluid, to a data logger, or to a printer (none of these devices are shown).

If membrane 18 becomes faulty (for example, if membrane 18 becomes fouled with a coating of material that interferes with oxygen permeability), the rate of oxygen diffusion across membrane 18 slows, thereby decreasing the steady-state signal produced by measurement electrode 12 so that it no longer accurately represents the oxygen level of the process fluid. To enable analyzer 10 to diagnose membrane fouling, processor 32 periodically commands controller 24 to briefly energize test electrode 14 (by inserting test electrode 14 into the circuit of auxiliary electrode 20 in place of measurement electrode 12). Test electrode 14 is energized sufficiently briefly (e.g., on the order of 10 seconds) so that its current response does not reach a steady-state level. As a result, the oxygen level measured by test electrode 14 is the equilibrium level of the oxygen established in electrolyte 16 during the time that measurement electrode 12 was energized, rather than the rate of oxygen diffusion across membrane 18. Thus, any fouling of membrane 18 does not appreciably degrade the current level produced by electrode 14. Accordingly, processor 32 determines whether membrane 18 has become fouled by comparing the signal produced by test electrode 14 with the oxygen level as measured with electrode 12 in a manner described in detail below.

If the signal produced by test electrode 14 indicates that the process fluid contains an appreciably greater level of oxygen than that indicated by the steady-state current level produced by measurement electrode 12, processor 32 determines that membrane 18 has become fouled and alerts the user by generating an alarm 36. Alarm 36 may be visual (for example, processor 32 may alter the oxygen level display 34 from a continuous to a blinking signal). In addition (or alternatively), alarm 36 may be audible, such as a tone 38. The user can respond to the alarm by either cleaning membrane 18 or replacing it with a new membrane.

Figure 2:
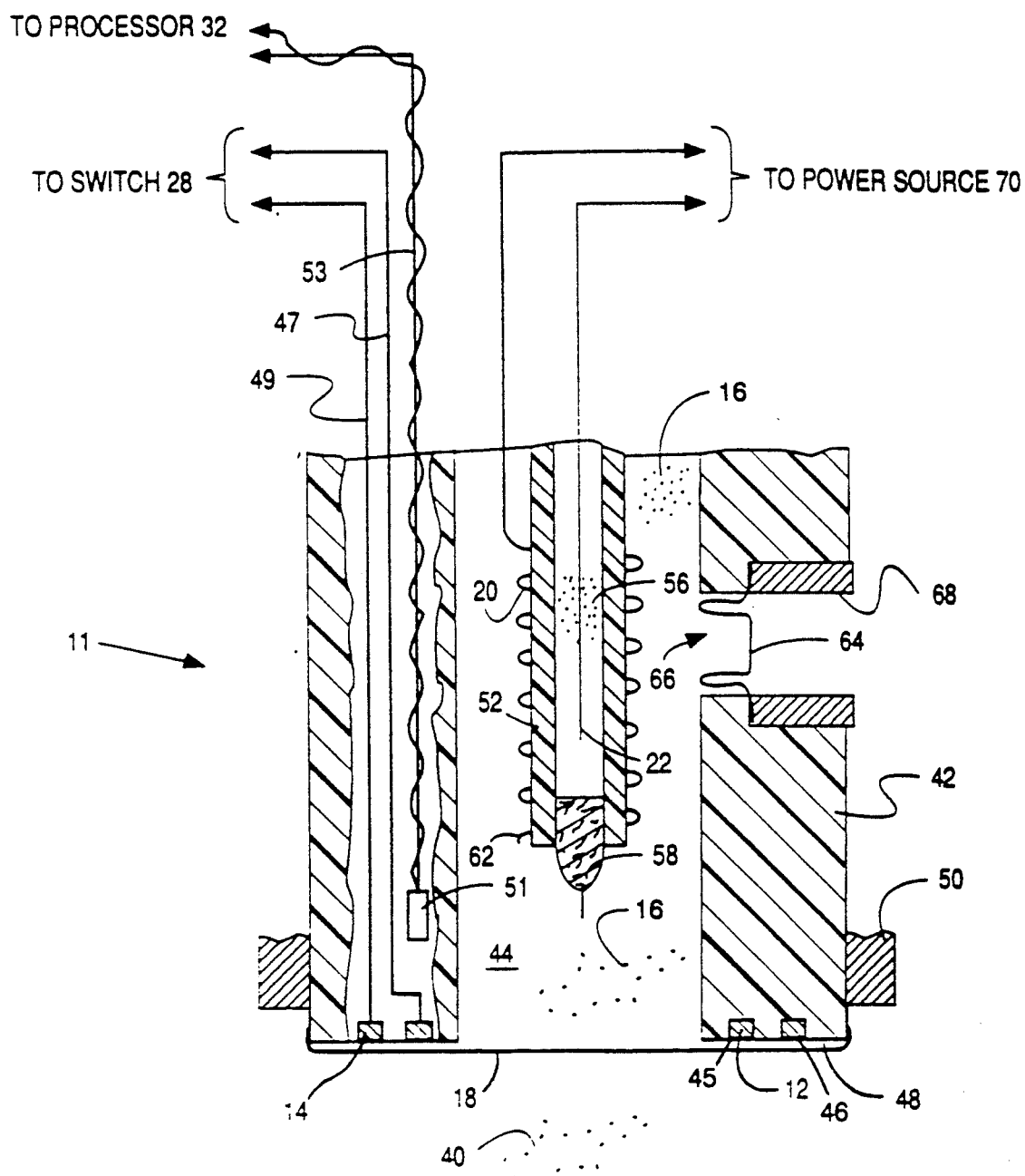
FIG. 2 is a partial cross-sectional view of a portion of the sensor of the chemical analyzer of FIG. 1.
Figure 3:
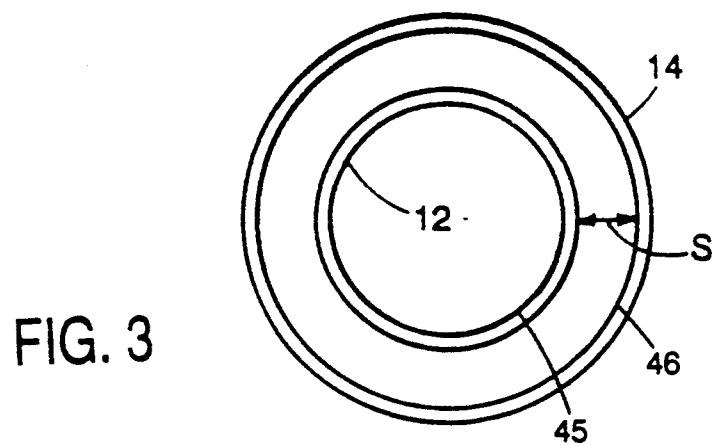
FIG. 3 is an end view of the sensor of FIG. 2 that shows the arrangement of two of the electrodes of the sensor.

Referring to FIGS. 2 and 3, the end of sensor 11 that is constructed to be inserted into process fluid 40 is shown in detail. Sensor 11 includes a hollow housing 42 made from Kynar ®, a plastic PVDF (poly vinylidene difluoride) commercially available from the Penwalt Corporation. The distal end of housing 42 supports a pair of coaxial gold or platinum rings that comprise measurement electrode 12 and test electrode 14, respectively. Measurement electrode 12, is disposed radially inwardly of test electrode 14, but the positions of electrodes 12, 14 may of course be reversed. A cavity 44 of housing is filled with elec solution 16 which is, for example, a 2 molar KCl (potassium chloride) that supports the electrochemical reaction of oxygen at electrodes 12, 14. Solution 16 may also include a surfactant and an algicide.

Membrane 18 is stretched tightly over the face 48 of housing 42 in which electrodes 12, 14 are embedded and is secured in place by a collar 50 that is attached to housing 42 with threads (not shown). Membrane 18 is thin (e.g., between 0.5 mils and 5 mils thick) and is made from any suitable material that is highly permeable to oxygen. For example, membrane 18 is Teflon ®, silicone rubber, or polyethylene. The spacing between membrane 18 and electrodes 12, 14, is quite narrow (and is shown greatly exaggerated for purposes of illustration) but is sufficient to allow a thin film of electrolyte solution 16 to form therebetween by capillary action.

A spacing S (e.g., ⅛ inch) separates measurement electrode 12 and test electrode 14 so that electrodes 12, 14 are exposed to different annular regions 45, 46 of a the film of electrolyte solution 16. When measurement electrode 12 is energized, oxygen that permeates membrane 18 into the film of electrolyte 16 in region 45 is electrochemically consumed as the oxygen reaches measurement electrode 14. Because test electrode 14 is de-energized during this time, oxygen that diffuses through membrane 18 into annular region 46 of electrolyte 16 is not consumed. Thus, the oxygen in region 46 is in equilibrium with the concentration of oxygen in process fluid 40. It is this level of oxygen that is measured when test electrode 14 is briefly energized to diagnose membrane fouling. The seal between membrane 18 and housing 42 and the energization of measurement electrode 12 serve to avoid lateral diffusion of oxygen to test electrode 14 from fluid 40 and the electrolyte in cavity 44, respectively.

The walls of housing 42 are hollow to accommodate wires 47, 49 that provide the electrical connections between switch 28 (FIG. 1) electrodes 12, 14, respectively. In addition, a thermistor 51 is suspended near the distal end of housing 42 by a pair of wires 53. Processor 32 (FIG. 1) uses the temperature measurement of electrolyte 16 provided by thermistor 51 (which indicates the temperature of fluid 40) to apply temperature correction to the oxygen level measurement, as described below.

A tube 52 is suspended within chamber 44 and supports reference electrode 22 (FIG. 1), which is a silver wire coated with silver chloride immersed in an electrolyte solution 56 of KCl. A porous ceramic wick 58 mounted in the distal end of tube 52 maintains electrolytic contact between solutions 16 and 56, and limits the internal diffusion of KCl between chamber 44 and the interior of tube 52. As explained below, this allows reference electrode 22 to be used to control the potential at electrodes 12, 14 when electrodes 12, 14 are energized.

Auxiliary electrode 20 (FIG. 1) is a silver wire in the form of a coil that is wrapped around tube 52 (only a portion of each winding is shown for clarity). The end 62 of the silver wire that forms auxiliary electrode 20 is disposed adjacent to the distal end of tube 52. Silver is used to avoid adding oxygen to electrolyte 16 (which would occur if material such as platinum or gold were to be used for electrode 20 and would disrupt the measurement) when auxiliary electrode 20 oxidizes during operation.

A pressure relief diaphragm 64 is held over a side opening 66 in chamber 44 by a plug 68. Diaphragm 64 is held at a much lower tension than membrane 18 so that diaphragm 64 expands and contracts preferentially to membrane 18 in response to changes in the pressure of electrolyte 16. For example, a gaseous bubble (not shown) trapped in cavity 44 will cause diaphragm 64 rather than membrane 18 to expand in response to temperature changes or pressure (depth of immersion) variations experienced by sensor 11. This helps maintain a constant spacing between membrane 18 and electrodes 12, 14 despite pressure changes in electrolyte 16. Because the rate of oxygen diffusion of from process fluid 40 to electrodes 12, 14 is a function of the spacing of membrane 18, a nonvariable spacing is critical to the accuracy of the oxygen level measurement.

Referring also to FIG. 1, auxiliary electrode 20 and reference electrode 22 are connected to a power source 70 that controls the level of current applied to the energized electrodes 12, 14. Energizing current for electrodes 12, 14 is provided by a D.C. voltage source 72 via a current driver 74. The polarity of the voltage applied by source 72 is selected to polarize electrodes 12, 14 in the cathodic direction. The current response of electrodes 12, 14 is linear with respect to the oxygen level in process fluid 40 when electrodes 12, 14 are energized at a potential of between about $-0.6$ volts and $-1.5$ volts with respect to reference electrode 22. Reference electrode 22 provides (through a high impedance voltage follower 76) negative feedback for driver 74 to maintain each electrode 12, 14 squarely within its linear range when energized (e.g., at a potential of $-0.7$ volts with respect to reference electrode 22).

Figure 4:
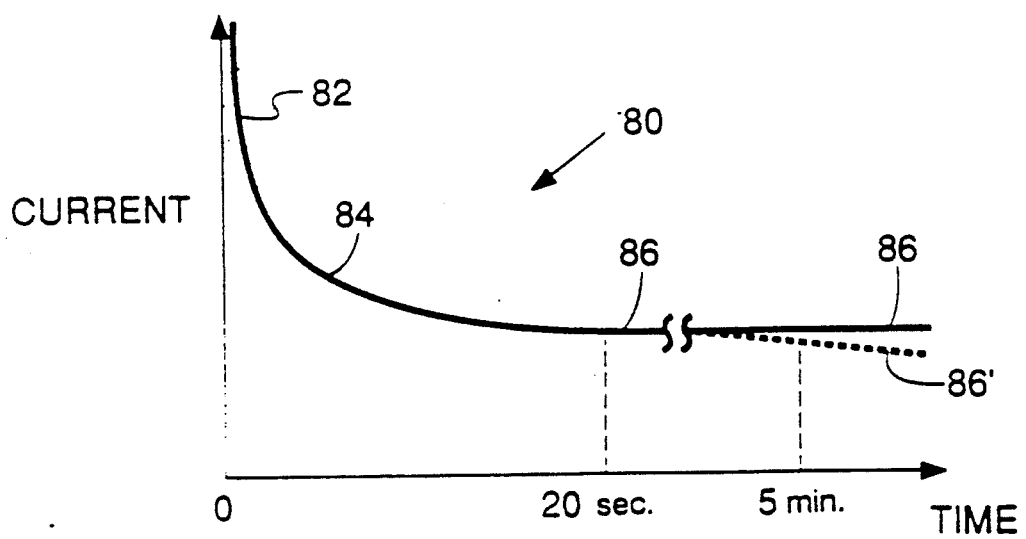
FIG. 4 illustrates the current-time response of one of the electrodes of the sensor of FIGS. 1 and 2.

Referring to FIG. 4, in operation, processor 32 begins the measurement process at time t=0 by commanding controller 24 to connect measurement electrode 12 to current to voltage converter 26 through switch 28, thereby completing the circuit with auxiliary electrode 20 and energizing measurement electrode 12. The oxygen concentration at the surface of electrode 12 is immediately driven to zero as the $O_2$ at the surface of electrode 12 is faradaically reduced to $OH^-$ according to the following equation:

$$O_2 + 2H_2O + 4e^- \rightarrow 4OH^-$$

As a result, immediately after time 0, measurement electrode 12 produces a high level of current that decays to a steady-state level according to curve 80. As shown by region 82 of curve 80, the current is initially capacitive (due to the charging of the double-charge layer at the surface of measurement electrode 12) as well as faradaic (due to the reduction of oxygen present at the surface of electrode 12). The immediate exhaustion of oxygen at the surface of electrode 12 causes oxygen to begin diffusing from process fluid 40 to electrolyte 16 across membrane 18, thereby slowing the rate of current decay. The current level continues to fall (as shown in region 84 of curve 80) and ultimately reaches a steady-state value that is proportional to the oxygen concentration gradient established across membrane 18 in region 45 of electrolyte 16.

The current reaches its steady-state value approximately 20 seconds after electrode 12 is energized. At this time, the rate at which electrode 12 reduces oxygen to $OH^-$ becomes fixed by the rate of oxygen diffusion across membrane 18 and is linearly proportional to the amount of oxygen in process fluid 40. Thereafter, in the absence of a fault (such as fouling of membrane 18) or a change in the oxygen level of fluid 40, the current level produced by electrode 12 will remain constant, as shown by region 86 of curve 80.

Processor 32 measures the steady-state current produced by electrode 12. As a result, processor 32 waits for about 1 minute after time 0 before beginning to analyze the signals from electrode 12. The analog current produced by measurement electrode 12 is converted to a voltage by current to voltage converter 26, and this voltage is repeatedly sampled and digitized by A/D converter 30. Processor 32 controls A/D converter 30 to sample the analog voltage every 33 milliseconds, but of course other sampling periods may be employed.

Processor 32 converts the values (i.e., the amplitudes) of the digital samples to derive the oxygen concentration (in parts per million, ppm) of fluid 40 by applying a constant of proportionality to the values. (The relationship between current and oxygen concentration is described in *Measurement of Dissolved Oxygen*, by Michael L. Hitchman, John Wiley & Sons, 1978.) Because the temperature of sample 40 affects the current produced by electrode 12, processor applies a temperature correction factor (stored in a table 88 in memory 33) to the derived oxygen concentration based on the temperature measured by thermistor 51. (The circuitry for digitizing the thermistor signal is not shown.) The temperature-compensated oxygen level can then be displayed 34 as a concentration of oxygen in ppm, or alternatively processor 32 may convert the oxygen level to another unit of measurement (such as percent saturation) and display the same. Periodically, or upon user command from an input 37 (such as a keypad on the front panel), processor 32 sends the temperature measurement to display 34 in place of the oxygen level.

Because the steady-state current 86 produced by measurement electrode 12 is a function of the rate at which oxygen diffuses across membrane 18, steady-state current 86 will decrease if the diffusion of oxygen is hampered. For example, oxygen-impermeable material (e.g., dirt, algae, oil, etc.) in process fluid 40 that collect on membrane 18 interfere with the diffusion of oxygen, thereby "fouling" membrane 18 and decreasing the current produced by electrode 12 so that the current no longer accurately reflects the oxygen concentration in fluid 40. This is shown by dashed portion 86' of current curve 80 in FIG. 4. The problem of fouling is particularly acute in applications in which sensor 10 is used with highly contaminated process fluids 40 (such as waste water in sewage treatment plants).

Figure 5:
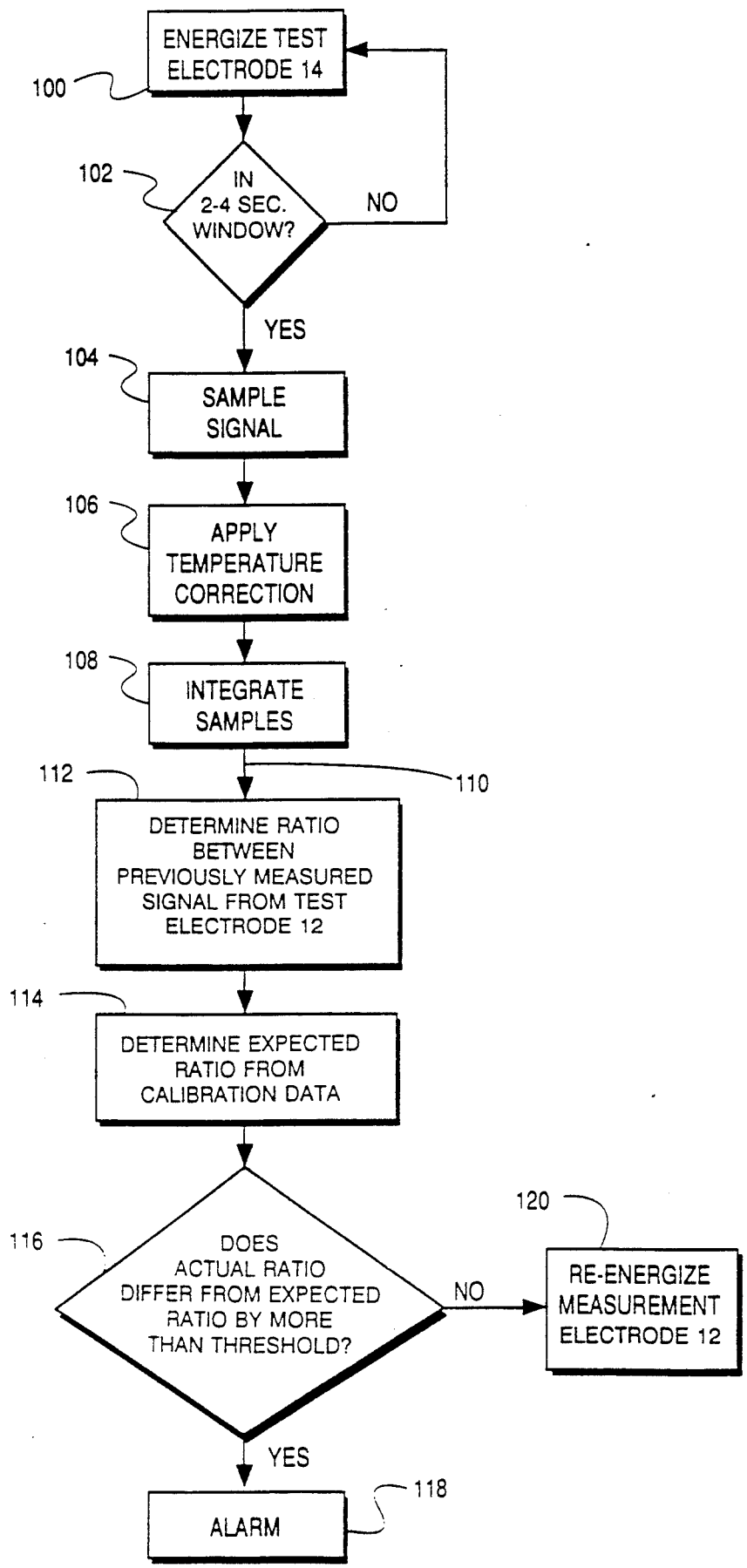
FIG. 5 is a flow chart useful in understanding how the analyzer of FIG. 1. diagnoses membrane fouling.

Referring also to FIG. 5, processor 32 periodically commands controller 24 to briefly energize test electrode 14 via switch 28 in place of measurement electrode 12 (step 100) and analyzes the resulting signal produced by test electrode 14 to determine whether membrane 18 has become fouled. The user can adjust the intervals between successive energizations (e.g., 15 minutes to 1 hour or more) as well as the duration of time that test electrode 14 is energized via input 37. The duration that test electrode 14 is energized should be insufficient for the current response of test electrode 14 to reach a steady-state level, and should also be sufficiently brief that measurement electrode 12 does not become discharged before it is re-energized by controller 24 (thereby allowing measurement electrode 12 to rapidly return to its steady state response when it is re-energized). Energizing test electrode 14 for 10 seconds between successive energizations of measurement electrode 12 has been found to be satisfactory for these purposes.

Figure 6:
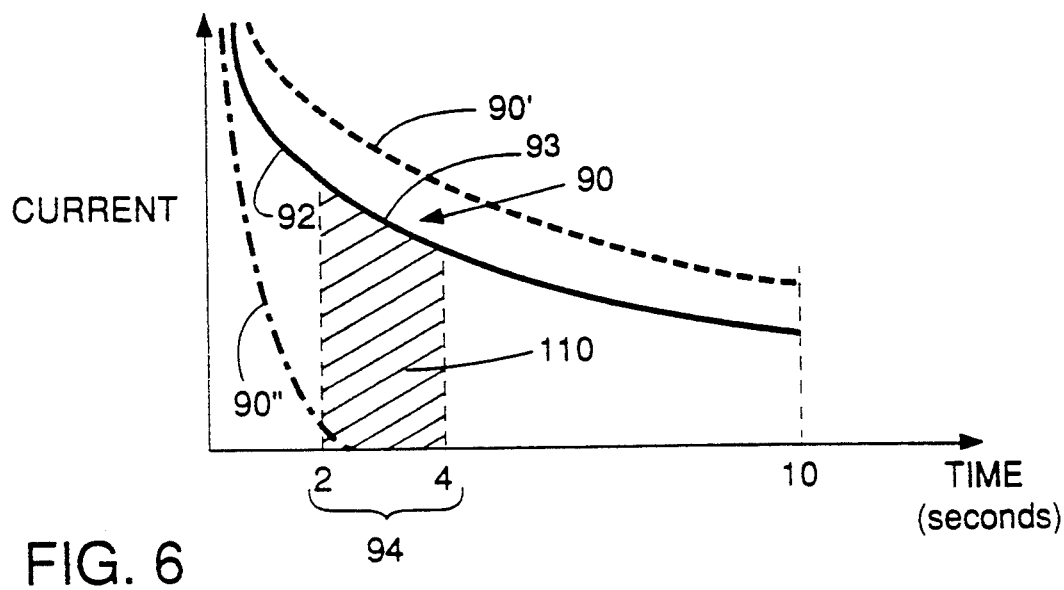
FIG. 6 illustrates the current-time response of another electrode of the sensor of FIGS. 1 and 2.

Referring also to FIG. 6, curve 90 illustrates the current response of test electrode 14. Because of the spacing between electrodes 12, 14, the oxygen concentration gradient established in region 45 of electrolyte by the steady-state operation of measurement electrode 12 does not deplete the level of oxygen in region 46 of electrolyte 16 disposed between test electrode 14 and membrane 18. Thus, immediately prior to the time that test electrode 14 is energized, the oxygen level in electrolyte region 46 is at equilibrium with the level of oxygen in fluid 40.

As explained above, immediately after test electrode 14 is energized, the oxygen at the surface of test electrode 14 is depleted, causing electrode 14 to produce a high level of current that decreases toward a steady state level as oxygen diffuses across membrane 18. For the first second or so after test electrode 14 is energized (region 92 of curve 90), the current has a large capacitive component and is ignored by processor 32. After this interval and before the steady-state current level is reached, the amount of current produced by test electrode 14 is a function of the rate at which the oxygen is exhausted in region 46 of electrolyte between test electrode 14 and membrane 18, as shown by region 93 of curve 90. Curve 90 represents approximately a 50% oxygen saturated sample. (For comparison, curve 90' shows the current response for a 100% oxygen saturated sample 40, while a sample 40 that contains no oxygen results in a current response shown by curve 90".)

Processor 32 analyzes the current produced by test electrode 14 during a portion of the time period that electrode 14 is energized, for example, during time window 94 of between 2 seconds and 4 seconds of the 10 second duration that electrode 14 is energized (step 102). During time window 94, A/D converter 30 provides processor 32 with about 60 samples (step 104) (at the 33 millisecond sampling rate) of the voltage produced by converter 26 in response to the current from test electrode 14. Processor 32 applies temperature correction (step 106) to the values of the samples (using stored table 88) and then integrates (step 108) the samples by adding them together and dividing the sum by the number of samples. The result corresponds to the total charge (in Coulombs) 110 gathered by test electrode 14 during the 2-4 second time window.

Due to the relatively brief interval that test electrode 14 is energized, the current produced by test electrode 14 does not reach a steady-state level and thus is not affected by the rate at which oxygen diffuses through membrane 18 into electrolyte region 46. As a result, applicant has found that total charge 110 is substantially independent of the degree of fouling of membrane 18. That is, for a given oxygen concentration of process fluid 40, total charge 110 will be substantially the same independently of whether membrane 18 is completely clean or is fouled. Thus, by comparing total charge 110 with the previously obtained steady state oxygen level measurement from measurement electrode 12 in the manner described below, processor 32 determines whether membrane 18 has become fouled and, if so, notifies the user by activating alarm 38.

Total charge 110 will rarely, if ever, equal the previously obtained steady state oxygen level measurement and in fact should exceed it. Applicant has found that the difference between total charge 110 and the steady state oxygen level measurement increases as membrane 18 becomes fouled. The reason is that fouling causes the steady-state current produced by measurement electrode 12 to decrease (as shown by curve 86' in FIG. 5) but does not cause a similar reduction in total charge 110, as discussed above. Thus, processor 32 determines the ratio between total charge 110 and the previously-obtained steady-state measurement of the oxygen level (step 112), and compares the actual ratio with the ratio that would be expected for a non-fouled electrode (steps 114, 116). If the actual ratio differs from the expected ratio by more than a threshold amount, processor 32 determines that membrane 18 has become fouled.

Figure 7:
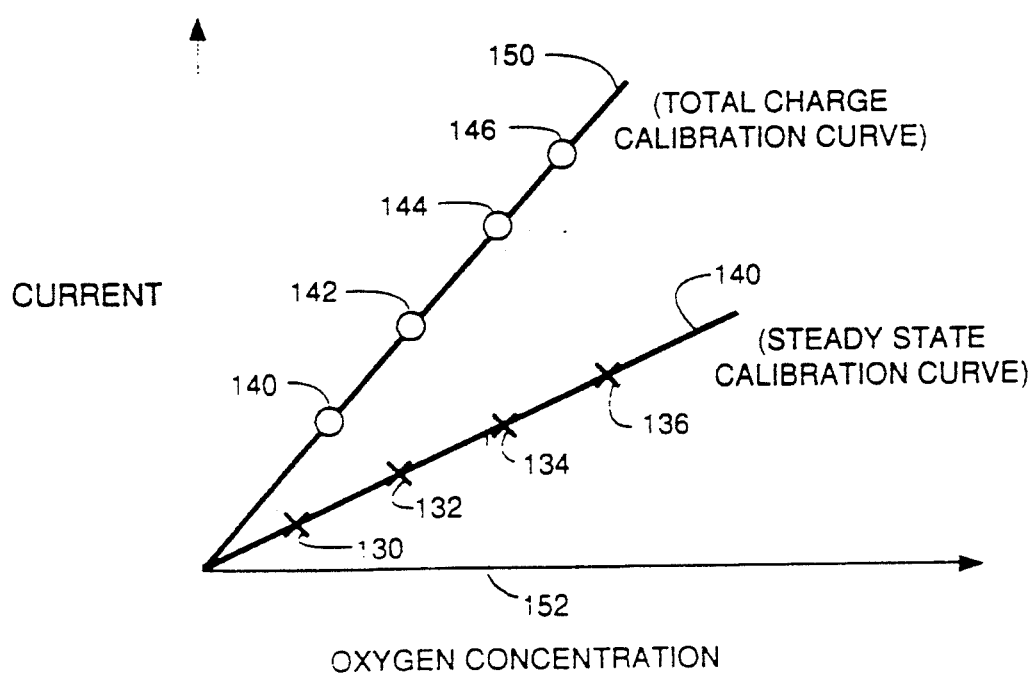
FIG. 7 shows a calibration chart useful in understanding how membrane fouling is diagnosed.

Referring to FIG. 7, processor 32 determines the expected ratios between total charge 110 and the steady state oxygen level measurements as a result of calibration of analyzer 10 with a clean membrane 18. During calibration, analyzer 10 makes a series of (e.g., four) steady-state measurements 130, 132, 134, 136 of the oxygen concentration of process fluid 40 using measurement electrode 12 in the manner described above. Each steady state measurement is made by energizing electrode 12 for 15 minutes. At the end of each 15 minute period, processor 32 stores the digitized, temperature corrected current from measurement electrode 12 in a working area 98 of memory 33 (FIG. 1). Steady state measurements 130-136 define a curve 140 that is linear with respect to the oxygen concentration of process fluid 40.

During calibration, analyzer 10 also performs a series of (e.g., 4) total charge measurements 140, 142, 144, 146 in the manner discussed above using test electrode 14. Total charge measurements 140-146 define a linear curve 150 with respect to oxygen concentration and are stored in working memory area 98. For any given concentration of oxygen in fluid 40 (such as concentration 152) the ratio between the total charge value on curve 150 and the steady state value on curve 140 defines the expected ratio used by processor 32 in step 116 (FIG. 5).

Thus, during operation, after processor 32 determines (step 112) the actual ratio between total charge 110 and the previously measured oxygen concentration, processor 32 determines (step 114) the expected ratio for the previously measured oxygen concentration using the calibration data stored in working memory area 98. The linearity of curves 140, 150 with respect to oxygen concentration makes this a relatively straightforward calculation. If the expected ratio exceeds the actual ratio by a threshold of, e.g., 30%, processor 32 determines that membrane 18 has become fouled and activates the alarm (step 118). Otherwise, processor commands controller 24 to re-energize electrode 12 (step 120) to begin the next measurement period.

The 30% threshold can be made stricter (e.g., reduced to 10% or less) or larger (e.g., increased to 50% or more), depending upon the tolerance to fouling that the user desires. Requiring a closer match between the expected and actual ratios will obviously alert the user when only a small amount of fouling has occurred. This may be advantageous in applications in which inaccuracies caused by even minor fouling are not desirable. In other, less stringent applications, the threshold may be increased so that the user is alerted only when membrane 18 is severely fouled.

Other embodiments are within the scope of the following claims.

For example, analyzer 10 can be used to measure the levels of chemicals other than oxygen by selecting suitable electrolyte and electrode materials. Fouling diagnoses can be based on the differences between the expected values on curves 140, 150, rather than their ratios.

Electrodes 12, 14 need not be energized for mutually exclusive time intervals.

Processor 32 can alternatively use the fouling determination to correct the oxygen level measurement.

Analyzer 10 can also perform other fault diagnoses.

Figure 8:
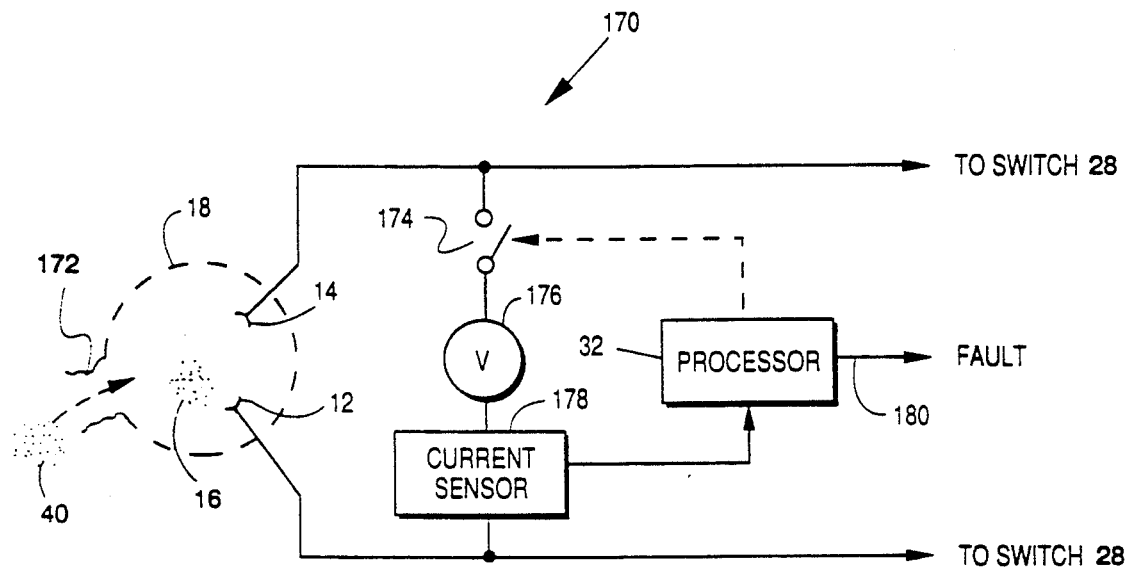
FIG. 8 is a functional block diagram of circuitry for detecting a rupture in the membrane of the sensor of FIGS. 1 and 2.

For example, referring to FIG. 8, circuitry 170 enables processor 32 to detect a rupture 172 in membrane 18 by detecting changes in the electrical resistance between electrodes 12, 14. The resistance presented by electrolyte 16 (e.g., 2 molar KCl) is approximately 300 ohms. A rupture 172 in membrane 18 would permit some of process fluid 40 (which is, e.g., waste water) to mix with electrolyte 16, thereby altering the resistance between electrodes 12, 14.

After each time window 94 (FIG. 6) but while test electrode 14 is energized, processor 32 closes a switch 174 to apply an A.C. voltage from a source 176 across electrodes 12, 14. The voltage produced by source 176 is at a relatively high frequency (1000 Hz) and is small (100 mV) so as not to interfere with the current response of either electrode. The resulting current between electrodes 12, 14 is measured by sensor 178, and the measurement is digitized (not shown) and applied to processor 32. Processor 32 applies temperature correction to the current level according to the temperature measured by thermistor 51. (Temperature correction may be omitted, if desired.) If the resistance indicated by the current differs from 300 ohms by more than a threshold amount (e.g., is outside of the range of 100 ohms to 1000 ohms), processor 32 generates a fault 180, which is displayed as an error message on display 34 (FIG. 1).

Because the resistance measurement is made after the current from test electrode 14 has been collected during time window 94, it does not interfere with the fouling diagnosis. Moreover, processor 32 opens switch 174 as soon as the resistance measurement has been completed (which takes one second or less). Thus, circuitry 170 is disconnected before measurement electrode 12 is re-energized.

Figure 9:
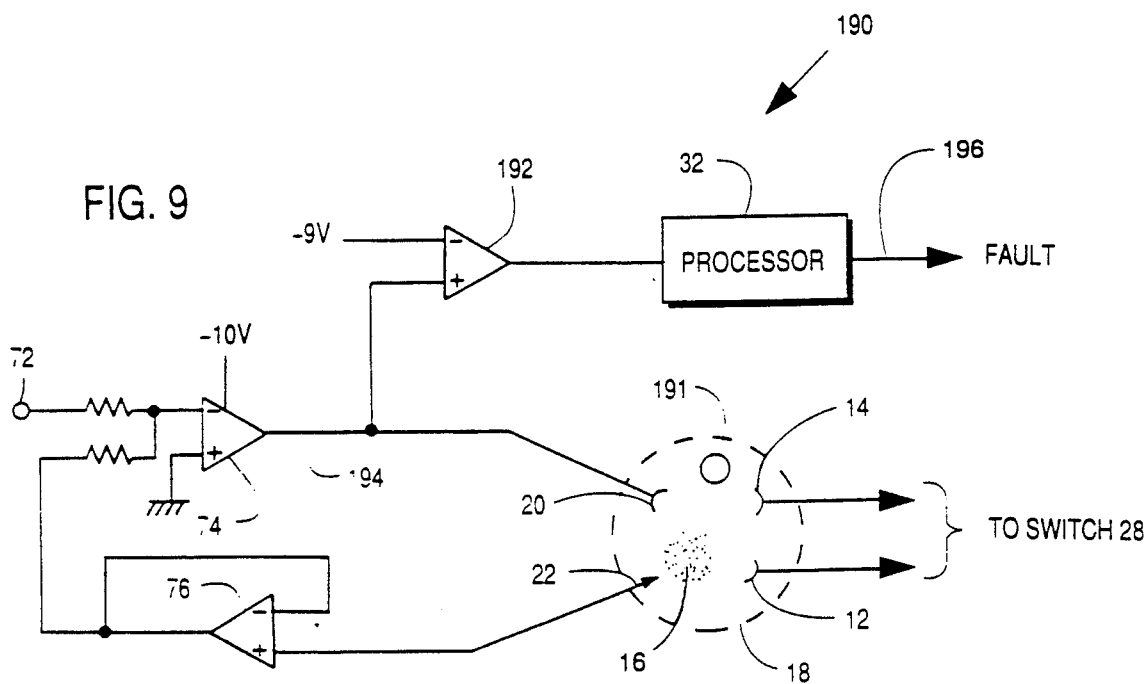
FIG. 9 is a functional block diagram of circuitry for detecting the presence of a gaseous bubble in the sensor of FIGS. 1 and 2.

Referring to FIG. 9, circuitry 190 detects loss of electrolytic solution 16 or the presence of one or more gaseous bubbles 191 in electrolyte 16. Although, as discussed above, pressure compensation diaphragm 64 (FIG. 2) helps maintain a fixed spacing between electrodes 12, 14 and membrane 18, the loss of electrolyte 16 or the presence of bubbles 191 in electrolytic solution 16 has other harmful effects. For example, loss of electrolyte 16 or the addition of gaseous bubbles increase the electrical resistance of the electrical path between auxiliary electrode 20 and measurement electrode 12 (or test electrode through electrolyte 16, thereby requiring the output voltage produced by current driver 74 to increase to maintain each electrode 12, 4 when energized at the desired potential of −0.7 volts with respect to reference electrode 22. Of course, driver 74 cannot produce an output voltage that exceeds its supply voltage (e.g., +10 volts). When this maximum level is reached, driver 74 will be unable to compensate for further increases in the resistance of electrolyte 16. If this occurs, the potential on energized electrodes 12, 14 will fall, leading to errors in the oxygen measurement or fouling diagnosis.

Comparator 192 monitors the output voltage 194 of driver 74. If output voltage 194 exceeds a predetermined percentage (e.g., 90%) of the supply voltage (in this example, +9 volts), comparator 192 notifies processor 32. Processor 32 responds to this error by generating a fault 96, which is displayed as an error message on display 34.

Still other embodiments are within the scope of the following claims.

What is claimed is:

1. Apparatus for detecting a selected chemical in a fluid, comprising
   a plurality of electrodes separated from said fluid by a membrane that is permeable to said selected chemical, each of said electrodes when energized producing a signal in response to said selected chemical in said fluid,
   a power source for energizing said electrodes,
   means for determining a level of said selected chemical in said fluid based on said signal produced by a first one of said electrodes, and
   means for comparing said determined level with said signal produced by a second one of said electrodes, and means for detecting whether said membrane is faulty based on said comparing.

2. The apparatus of claim 1 further comprising means for analyzing said signal produced by said second electrode to derive an expected level of said selected chemical, and means for detecting that said membrane is faulty if said determined level differs from said expected level by more than a selected amount.

3. The apparatus of claim 2 further comprising a controller for causing said power source to energize said second electrode for a selected duration of time and for causing said means for analyzing to analyze said signal produced by said second electrode during a portion of said selected duration.

4. The apparatus of claim 3 wherein said controller causes said power source to energize said first electrode for a duration that exceeds said selected duration.

5. The apparatus of claim 4 wherein said controller causes said power source to energize said first electrode for a duration which causes said signal produced by said first electrode to reach a steady-state value.

6. The apparatus of claim 3 wherein said controller causes said power source to energize said first electrode and said second electrode for mutually exclusive intervals of time.

7. The apparatus of claim 4 wherein said controller includes means for causing said power source to energize said first electrode for a first duration which causes said signal produced by said first electrode to reach a steady-state value and means for causing said power source to energize said second electrode for a second duration which causes said signal produced by said second electrode to reach a steady-state value.

8. The apparatus of claim 7 wherein said first duration is greater than 1 minute.

9. The apparatus of claim 7 wherein said first duration is at least 15 minutes.

10. The apparatus of claim 7 wherein said second duration is on the order of 10 seconds and occurs between successive energizations of said first electrode.

11. The apparatus of claim 7 further comprising means for setting said first duration and said second duration.

12. The apparatus of claim 3 wherein said means for analyzing includes means for integrating said signal produced by said second electrode during said portion of said selected duration to produce said expected level.

13. The apparatus of claim 12 wherein said selected amount is based on a calibrated ratio between said determined level and said expected level.

14. The apparatus of claim 13 wherein said selected amount is between 10% and 50% of said calibrated ratio.

15. The apparatus of claim 13 further comprising means for generating an alarm if said means for detecting detects that said membrane is faulty.

16. The apparatus of claim 3 wherein said portion is less than said selected duration.

17. The apparatus of claim 1 wherein said membrane is subject to fouling when material in said fluid, to which said membrane is impermeable, collects on and reduces the permeability of said membrane to said selected chemical, said means for determining including means for detecting that said membrane is fouled when said determined level and said signal produced by said second electrode differ by more than a selected amount, and indicating that said fouled membrane is faulty.

18. The apparatus of claim 1 wherein said first electrode and said second electrode are disposed within a liquid electrolyte and are spaced by an amount which enables said electrodes to respond to said selected chemical in different regions of said electrolyte.

19. The apparatus of claim 18 wherein said first electrode and said second electrode are each annular and are disposed coaxially with respect to each other.

20. The apparatus of claim 1 wherein said selected chemical includes oxygen or an allotrope thereof.

21. The apparatus of claim 1 further comprising
circuitry for detecting an electrical resistance between said first electrode and said second electrode, and
means for determining that said membrane is fractured if said resistance differs from a reference resistance by a selected amount.

22. The apparatus of claim 21 further comprising a controller which causes said power source to energize said second electrode for a selected duration of time and said means for determining to analyze said signal produced by said second electrode during a portion of said selected duration to detect whether said membrane is faulty, said detecting circuitry detecting said resistance after said portion of said selected duration.

23. The apparatus of claim 1 wherein said power source includes a third electrode for supplying electrical current to energize said first electrode and said second electrode.

24. The apparatus of claim 23 wherein said first, second, and third electrodes are disposed in an electrolyte liquid that is enclosed by said membrane, and further comprising
circuitry for sensing a loss of said electrolyte liquid and activating an alarm to notify a user thereof.

25. The apparatus of claim 24 wherein said power source includes a driver for generating electrical current at an output thereof and applying said current to said third electrode, said sensing circuitry including circuitry for monitoring a voltage at said output and determining that said loss has occurred if said voltage exceeds a threshold.

26. The apparatus of claim 1 wherein said first and second electrodes are disposed in a cavity a portion of which is bounded by said membrane, and further comprising an electrolyte liquid disposed in said cavity at a selected pressure, and means are maintaining said electrolyte liquid at said selected pressure in response to changes in temperature of said electrolyte liquid.

27. The apparatus of claim 26 wherein said first and second electrodes are spaced by a selected distance from said membrane, and further comprising a diaphragm that bounds a second portion of said cavity, said diaphragm being maintained at a tension which is less than a tension of said membrane so that said diaphragm expands preferentially to said membrane in response to said changes in temperature, thereby to maintain said selected distance.

28. The apparatus of claim 23 wherein said power source further includes
a reference electrode disposed adjacent to first electrode and said second electrode, and
circuitry for controlling electrical power applied to said third electrode based on an electrical potential developed between said reference electrode and an energized one of said first electrode or said second electrode.

29. The apparatus of claim 1 further comprising
means for measuring a temperature of said fluid, and
means for correcting the level of said selected chemical determined by said determining means based on said temperature.

30. Apparatus for detecting a selected chemical in a fluid, comprising
a housing that is adapted to be inserted in said fluid, said housing having an end over which a membrane that is permeable to said selected chemical is disposed, said end having a surface disposed substantially parallel to said membrane for supporting a plurality of electrodes adjacent to said membrane and separated from said fluid by said membrane,
a first one of said electrodes being adapted to be energized for first duration of time which enables said first electrode to produce a first signal that indicates a level of said selected chemical in said fluid,
a second one of said electrodes being adapted to be energized for a second duration of time which enables said second electrode to produce a second signal that when compared with said first signal provides an indication of whether said membrane is faulty.

31. The apparatus of claim 30 further comprising means for energizing said first electrode so that said first duration of time enables said first signal to reach a steady-state value in response to said level of said selected chemical, and for energizing said second electrode so that said second duration does not enable said second signal to reach a steady-state value in response to said level of said selected chemical.

32. A method for detecting a selected chemical in a fluid, comprising
providing a plurality of electrodes separated from said fluid by a membrane that is permeable to said selected chemical, each of said electrodes when energized producing a signal in response to said selected chemical in the fluid,
energizing said electrodes,
determining a level of said selected chemical in said fluid based on said signal produced by a first one of said electrodes,
comparing said determined level with said signal produced by a second one of said electrodes, and
detecting whether said membrane is faulty based on said comparing.

33. The method of claim 32 further comprising
analyzing said signal produced by said second electrode to derive an expected level of said selected chemical, and
detecting that said membrane is faulty if said determined level differs from said expected level by more than a selected amount.

34. The method of claim 33 further comprising energizing said second electrode for a selected duration of time and analyzing said signal produced by said second electrode during a portion of said selected duration.

35. The method of claim 34 further comprising energizing said first electrode for a duration that exceeds said selected duration.

36. The method of claim 35 further comprising energizing said first electrode for a duration which causes said signal produced by said first electrode to reach a steady-state value.

37. The method of claim 34 further comprising energizing said first electrode and said second electrode for mutually exclusive intervals of time.

38. The method of claim 35 further comprising energizing said first electrode for a first duration which causes said signal produced by said first electrode to reach a steady-state value, and energizing said second electrode for a second duration which does not cause said signal produced by said second electrode to reach a steady-state value.

39. The method of claim 38 wherein said first duration is greater than 1 minute and said second duration is on the order of 10 seconds and occurs between successive energizations of said first electrode.

40. A method for detecting a selected chemical in a fluid, comprising providing a plurality of electrodes separated from said fluid by a membrane that is permeable to said selected chemical, each of said electrodes when energized producing a signal in response to said selected chemical in the fluid, energizing said first electrode for a first duration of time which causes said signal produced by said first electrode to reach a steady-state value, energizing said second electrode for a second duration of time which does not cause said signal produced by said second electrode to reach a steady-state value, said first duration exceeding said second duration, allowing a user of said apparatus to select said first duration and said second duration, determining a level of said selected chemical in said fluid based on said signal produced by a first one of said electrodes, analyzing said signal produced by said second electrode during said second duration to derive an expected level of said selected chemical, and detecting that said membrane is faulty if said determined level differs from said expected level by more than a selected amount.

41. The method of claim 34 wherein said step of analyzing includes integrating said signal produced by said second electrode during said portion of said selected duration to produce said expected level.

42. A method for detecting a selected chemical in a fluid, comprising providing a plurality of electrodes separated from said fluid by a membrane that is permeable to said selected chemical, each of said electrodes when energized producing a signal in response to said selected chemical in the fluid, energizing said electrodes, said step of energizing including energizing said second electrode for a selected duration of time, determining a level of said selected chemical in said fluid based on said signal produced by a first one of said electrodes, analyzing said signal produced by said second electrode during a portion of said selected duration to derive an expected level of said selected chemical, said step of analyzing including integrating said signal produced by said second electrode during said portion of said selected duration to produce said expected level, said section duration being based on a calibrated ratio between said determined level and said expected level, and detecting that said membrane is faulty if said determined level differs from said expected level by more than a selected amount.

43. The method of claim 42 wherein said selected amount is between 10% and 50% of said calibrated ratio.

44. The method of claim 42 further comprising generating an alarm if said means for detecting detects that said membrane is faulty.

45. The method of claim 34 wherein said portion is less than said selected duration.

46. The method of claim 32 wherein said membrane is subject to fouling if material in said fluid to which said membrane is impermeable collects on and reduces the permeability of said membrane to said selected chemical, said step of detecting including determining that said membrane is fouled when said determined level and said signal produced by said second electrode differ by more than a selected amount, and further comprising indicating that said fouled membrane is faulty.

47. A method for detecting a selected chemical in a fluid, comprising providing a plurality of electrodes separated from said fluid by a membrane that is permeable to said selected chemical, each of said electrodes when energized producing a signal in response to said selected chemical in the fluid, energizing a first one of said electrodes for a time which causes said signal produced thereby in response to said selected chemical to reach a steady-state value and determining a level of said selected chemical based on said signal produced by said first electrode, energizing a second one of said electrodes for a time which does not cause said signal produced thereby in response to said selected chemical to reach a steady-state value, and detecting whether said membrane is faulty based on comparing said signal produced by said second electrode with said determined level.

* * * * *